(12) United States Patent
Gott et al.

(10) Patent No.: US 6,638,527 B2
(45) Date of Patent: Oct. 28, 2003

(54) SUBSTANTIALLY DRY CLEANSING PRODUCT OF IMPROVED LATHERABILITY AND WET FLEXIBILITY

(75) Inventors: Robert Edward Gott, Norwalk, CT (US); Filomena Augusta Gomes, Naugatuck, CT (US); Craig Stephen Slavtcheff, Guilford, CT (US); Walter Joseph Lunsmann, Ringoes, NJ (US)

(73) Assignee: Unilever Home & Personal Care USA, division of Conopco, Inc., Greenwich, CT (US)

( * ) Notice: Subject to any disclaimer, the term of this patent is extended or adjusted under 35 U.S.C. 154(b) by 111 days.

(21) Appl. No.: 09/829,374

(22) Filed: Apr. 9, 2001

(65) Prior Publication Data

US 2001/0046513 A1 Nov. 29, 2001

Related U.S. Application Data

(60) Provisional application No. 60/197,480, filed on Apr. 17, 2000.

(51) Int. Cl.$^7$ .......................... A61K 7/00; A61F 13/00
(52) U.S. Cl. ........................ 424/443; 424/401
(58) Field of Search ................ 424/443, 401, 424/446, 400

(56) References Cited

U.S. PATENT DOCUMENTS

| | | |
|---|---|---|
| 5,863,663 A | 1/1999 | Mackey et al. |
| 5,951,991 A | 9/1999 | Wagner et al. |
| 5,952,043 A | 9/1999 | Mackey et al. |
| 5,972,361 A | 10/1999 | Fowler et al. |
| 5,980,931 A | 11/1999 | Fowler et al. |
| 6,063,397 A | 5/2000 | Fowler et al. |
| 6,074,655 A | 6/2000 | Fowler et al. |
| 6,103,644 A | 8/2000 | Sheridan |
| 6,132,746 A | 10/2000 | Hasenoehrl et al. |
| 6,190,678 B1 | 2/2001 | Hasenoehrl et al. |

FOREIGN PATENT DOCUMENTS

| | | |
|---|---|---|
| EP | 0066463 A | 5/1982 |
| EP | 0 459 821 A2 | 12/1991 |
| EP | 0 763 341 A1 | 3/1997 |
| EP | 0 870 496 | 10/1998 |
| FR | 2 331 980 | 6/1977 |
| GB | 1 473 147 | 5/1977 |
| WO | 97/45256 | 12/1997 |
| WO | 99/55303 | 11/1999 |
| WO | 99/63963 | 12/1999 |
| WO | 01/08640 | 2/2001 |
| WO | 01/08641 | 2/2001 |
| WO | 01/08655 | 2/2001 |
| WO | 01/08656 | 2/2001 |
| WO | 01/08657 | 2/2001 |
| WO | 01/08658 | 2/2001 |
| WO | 01/78679 | 10/2001 |

OTHER PUBLICATIONS

GB Search Report, GB 0108573.7 Sep. 26, 2001—1 page.
International Search Report No. PCT/EP 01/03836 dated Feb. 25, 2002, 5 pp.
WPI 1977–51501Y/197729 Derwent Abstract of Patent No. FR 2331980, 1 p.
French Search Report No. FR 0105115.

*Primary Examiner*—James M. Spear
(74) *Attorney, Agent, or Firm*—Alan A. Bornstein

(57) ABSTRACT

A disposable, single-use, substantially dry cleansing article is disclosed having wet flexibility, and a lathering surfactant in one embodiment and having an apertured fabric and a specific lather volume coefficient in a second embodiment.

19 Claims, 4 Drawing Sheets

SUBSTANTIALLY DRY CLEANSING PRODUCT OF IMPROVED LATHERABILITY AND WET FLEXIBILITY

This application claims the benefit of U.S. provisional application No. 60/197,480 filed Apr. 17, 2000.

BACKGROUND

1. Field of the Invention

The invention relates to substantially dry, disposable, personal cleansing products.

2. Description of the Related Art

Personal cleansing products have traditionally been marketed in a variety of forms such as bar soaps, creams, lotions, and gels. These formulations have attempted to satisfy a number of criteria to be acceptable to consumers. These criteria include cleansing effectiveness, skin feel, skin mildness and lather volume. Ideal personal cleansers should gently cleanse the skin or hair, cause little or no irritation, and not leave the skin or hair overly dry after frequent use. Personal cleansing products have also been combined with water insoluble fibrous substrates to improve convenience to the user.

A series of granted and pending patent applications have been published by Procter & Gamble describing substantially dry, disposable, personal cleansing products which address many of the aforementioned functionality concerns. These products are substantially dry articles having deposited onto a woven or non-woven cloth a cleansing composition of surfactant, structurant, skin conditioning agent and other performance ingredients. U.S. Pat. No. 5,951,991 (Wagner et al.) focuses on providing the substrate with a conditioning emulsion separately impregnated from the lathering surfactant onto the cloth substrate. U.S. Pat. No. 5,980,931 (Fowler et al.) emphasizes impregnation of oil soluble conditioning agents. Manufacturing processes for these products are reported in U.S. Pat. No. 5,952,043 and U.S. Pat. No. 5,863,663, both to Mackey et al.

Unfortunately, the substantially dry disposable cleansing products disclosed in the prior art are generally unsuitable for cleansing the entire body for various reasons. One weakness of the prior art disposable wipes is that the wipe doesn't retain its shape well during cleansing after becoming saturated with water. This lack of shape memory causes the wipe to either roll up like a pencil or crumple into a small ball when in use which is especially problematic for a body washing application. Another problem is the deficient latherability found for very mild cleansing agents such as C12 to C24 fatty acids when used in conjunction with the prior art wipes.

The inventive wipe solves the problem of shape memory or "bounce-back" by employing a water insoluble substrate, lathering surfactant and structurant system which together unexpectedly provide "wet flexibility". Wet flexibility is herein defined as the surfactant impregnated wipe's ability to return to its original shape after being deformed while saturated with water. Substantially dry is herein defined as having a water content of less than about 0.15 weight ratio to the substrate. The inventive wipe further solves the problem of deficient lathering ability of mild cleansing agents, by the unexpected observation that the combination of such mild cleansing agents and an apertured fabric provides a substantial amount of lather during use. In a preferred embodiment, the inventive dry disposable cleansing wipe combines wet flexibility, a mild lathering surfactant, and a C5–C12 alkyl diol structurant system. More preferably, the inventive wipe will be treated with a coating solution containing C5–C12 diol/lathering surfactant ratio between 1 to 8 and 1 to 1. Most preferably, the water insoluble substrate in the inventive wipe has at least one apertured non-woven fabric layer.

SUMMARY OF THE INVENTION

This invention relates to a substantially dry, disposable, mild cleansing article for cleansing the body with a good lather comprising a water insoluble substrate having at least one apertured layer impregnated with a lathering surfactant, and the article having wet flexibility.

DETAILED DESCRIPTION OF THE INVENTION

Figure 1:
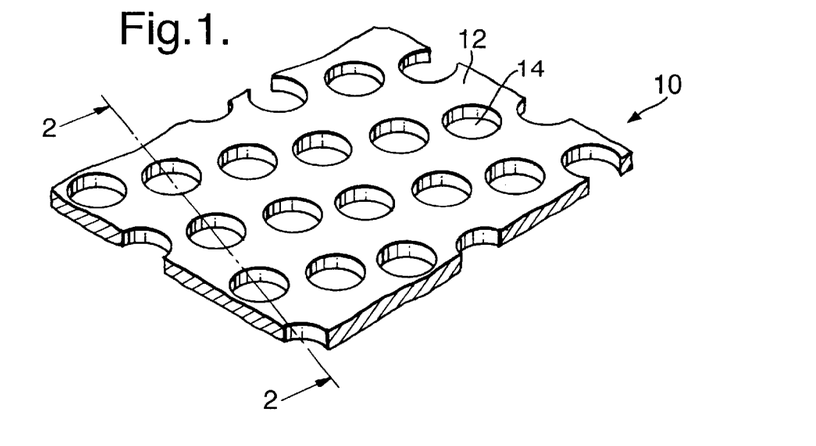
FIG. 1 is a perspective representation of one embodiment of the inventive cleansing article having a single layer apertured water insoluble substrate.

Referring now to the drawings in which like figures represent like elements, in FIG. 1, cleansing article 10 is made up of a water insoluble substrate or fabric 12 containing apertures 14 distributed in a uniform or non-uniform arrangement throughout fabric 12.

Figure 2:
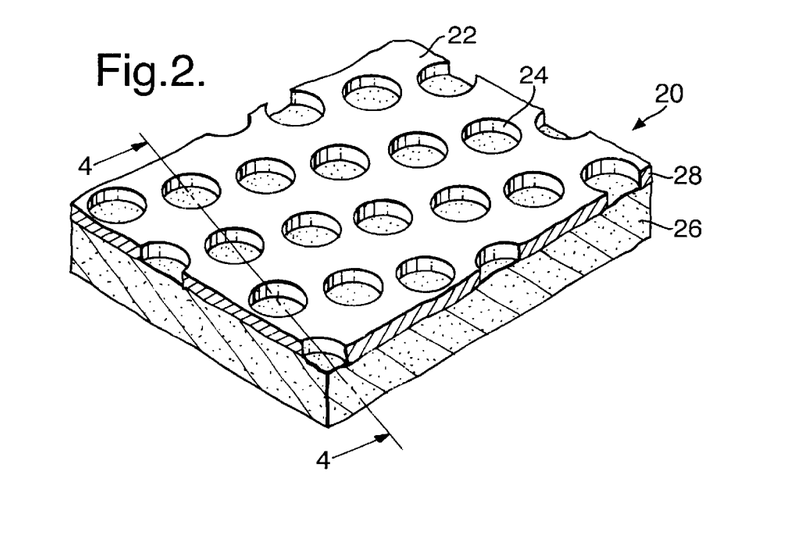
FIG. 2 is a perspective representation of another embodiment of the inventive cleansing article having two layers of an insoluble substrate bonded together.

Referring now to FIG. 2 cleansing article 20 contains first layer 22 laminated onto second layer 26 along interface 28. First layer 22 contains apertures 24 distributed either uniformly or non-uniformly throughout first layer 22. Second layer 26 is a non-apertured fabric having preferably a less dense arrangement of fibers than first layer 22.

Figure 3:
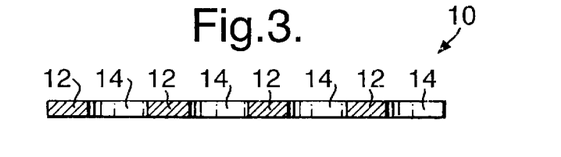
FIG. 3 is a cross-sectional view taken along line 2—2 of FIG. 1.

In FIG. 3, cleansing article 10 is shown along cross-section 2—2 depicted in FIG. 1.

Figure 4:
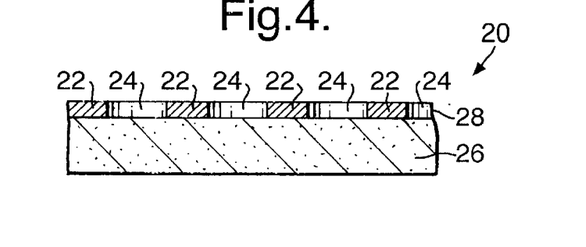
FIG. 4 is a cross-sectional view taken along line 4—4 of FIG. 2.

Now referring to FIG. 4 in which cleansing article 20 is shown along a cross section 4—4 depicted in FIG. 2. First layer 22 is laminated to second layer 26 along interface 28. First layer 22 also has apertures 24 distributed either uniformly or non-uniformly therethrough.

Figure 5A:
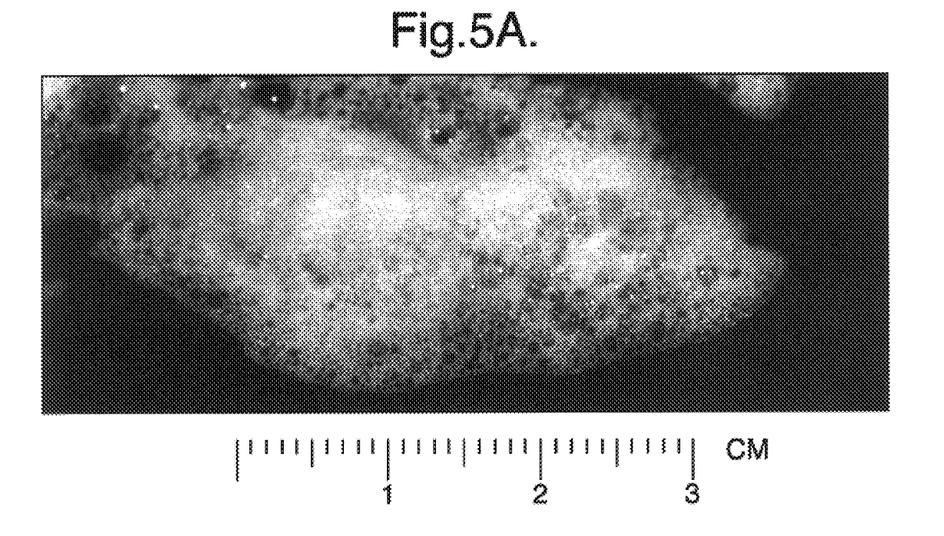
FIGS. 5(a) and (b) are photographs of the lather produced by two embodiments of the inventive cleansing article having a single layer apertured water insoluble substrate.

In FIG. 5(a), a rich, bubbly lather is depicted which is produced according to the lathering method described below by the inventive wipe comprising a single layer of 6 by 8 inch apertured PGI fabric coated with 0.75 gms of the composition described in Table 1.

Figure 5B:
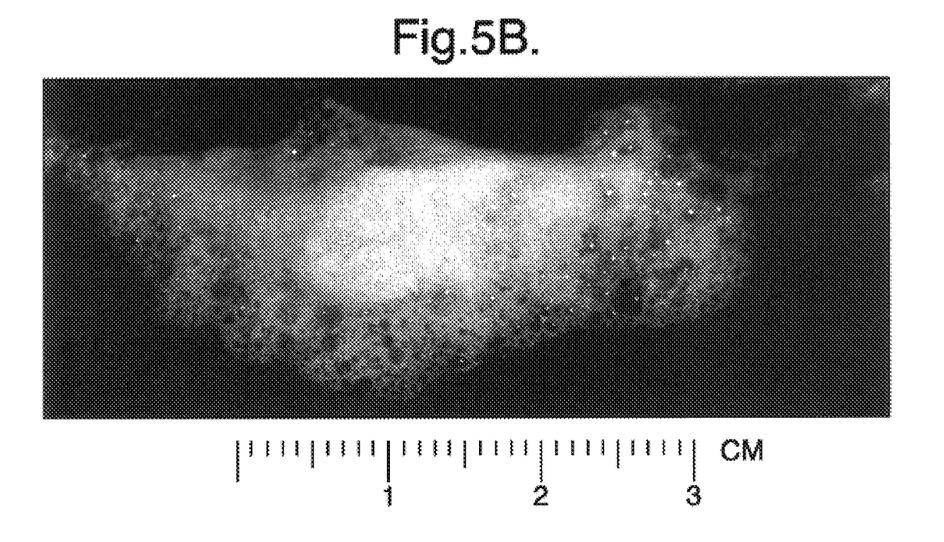

In FIG. 5(b), a rich, bubbly lather is depicted which is produced according to the lathering method described below by the inventive wipe comprising a single layer of 6 by 8 inch apertured PGI fabric coated with 0.75 gms of the composition described in Table 3.

Figure 5C:
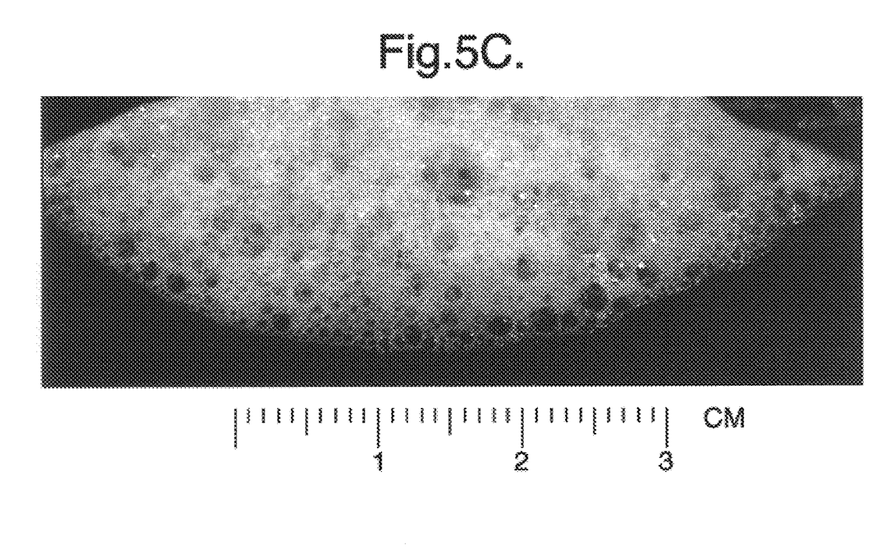
FIG. 5(c) is a photograph of the lather produced by an embodiment of a comparative cleansing article having a single layer apertured water insoluble substrate.

In FIG. 5(c), a loose, bubbly lather is depicted which is produced according to the lathering method described below by a comparative wipe comprising a single layer of 6 by 8 inch non-apertured CLC 062 fabric coated with 0.75 gms of the composition described in Table 1.

Figure 6A:
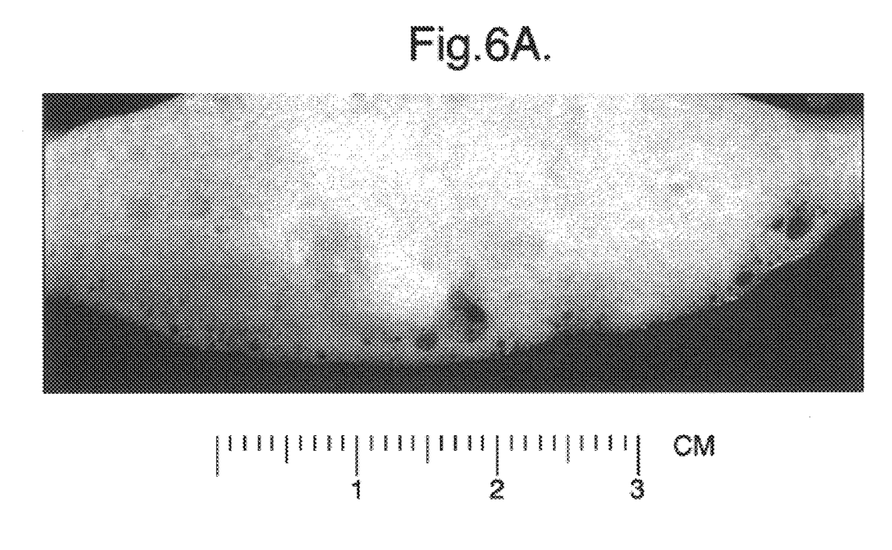
FIGS. 6(a) and (b) are photographs of the lather produced by two embodiments of the inventive cleansing article having two layers of an insoluble substrate bonded together.

In FIG. 6(a), a creamy, bubbly lather is depicted which is produced according to the lathering method described below by an inventive wipe comprising a single layer of 6 by 8 inch apertured PGI fabric coated with 4.8 gms of the composition described in Table 4, which is bonded to a single layer of Carlee high loft fabric.

Figure 6B:
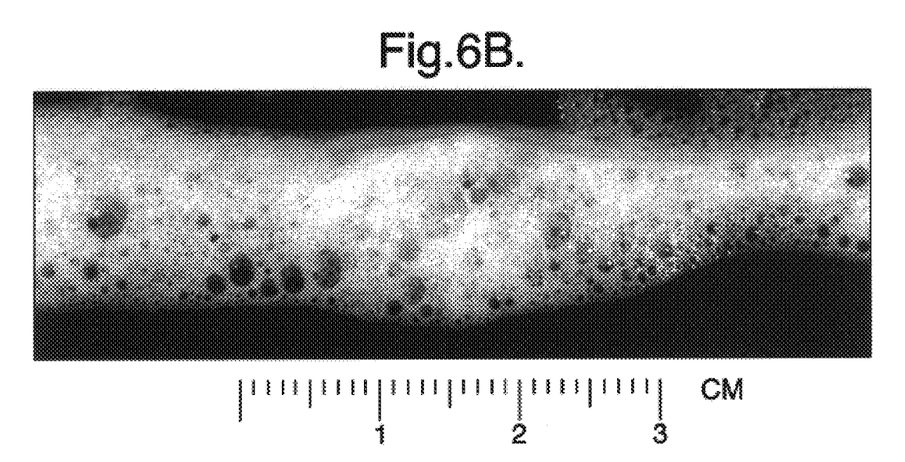

In FIG. 6(b), a creamy, bubbly lather is depicted which is produced according to the lathering method described below by an inventive wipe comprising a single layer of 6 by 8 inch apertured DuPont 8688 fabric coated with 4.8 gms of the composition described in Table 4, which is bonded to a single layer of Carlee high loft fabric.

Latherability:

The lather of the inventive articles is characterized by a rich or creamy appearance compared to the loose, bubbly or airy appearance of the lather of comparative wipes. The bubble diameter distribution of a rich or creamy lather is narrow, and substantially uniform, with the mean bubble diameter preferably below about 200 microns. In contrast, the bubble diameter distribution of a loose, bubbly or airy lather is wider, and substantially non-uniform, with the mean bubble diameter above about 200 microns, preferably above about 500 microns. The stability or persistence of the lather of the inventive wipes is also substantially greater than that of the lather of comparative wipes.

Water insoluble substrate:

The inventive dry wipe contains a water insoluble substrate as a component. By "water insoluble" is meant the substrate does not dissolve or readily break apart upon immersion in water. A wide variety of materials can be used as the substrate. The following non-limiting characteristics are desirable: (i) sufficient wet strength for use, (ii) sufficient abrasivity, (iii) sufficient loft and porosity, (iv) sufficient thickness, and (v) appropriate size.

Non-limiting examples of suitable insoluble substrates which meet the above criteria include non-woven substrates, woven substrates, hydro-entangled substrates, air entangled substrates and the like. Preferred embodiments employ non-woven substrates since they are economical and readily available in a variety of materials. By non-woven is meant that the layer is comprised of fibers which are not woven into a fabric but rather are formed into a sheet, particularly a tissue. The fibers can either be random (i.e., randomly aligned) or they can be carded (i.e. combed to be oriented in primarily one direction). Furthermore, the non-woven substrate can be composed of a combination of layers of random and carded fibers.

Non-woven substrates may be comprised of a variety of materials both natural and synthetic. By natural is meant that the materials are derived from plants, animals, insects or byproducts. By synthetic is meant that the materials are obtained primarily from various man-made materials or from material that is usually a fibrous web comprising any of the common synthetic or natural textile-length fibers, or mixtures thereof.

Non-limiting examples of natural materials useful as components in the present invention are silk fibers, keratin fibers and cellulosic fibers. Non-limiting examples of keratin fibers include those selected from the group consisting of wool fibers, camel hair fibers, and the like. Non-limiting examples of cellulosic fibers include those selected from the group consisting of wood pulp fibers, cotton fibers, hemp fibers, jute fibers, flax fibers, and mixtures thereof. Wood pulp fibers are preferred while all cotton fibers (e.g. cotton pads) are normally avoided.

Non-limiting examples of synthetic materials useful as components in the present invention include those selected from the group consisting of acetate fibers, acrylic fibers, cellulose ester fibers, modacrylic fibers, polyamide fibers, polyester fibers, polyolefin fibers, polyvinyl alcohol fibers, rayon fibers and mixtures thereof. Examples of some of these synthetic materials include acrylics such as Acrilan®, Creslan®, and the acrylonitrile-based fiber, Orlon®; cellulose ester fibers such as cellulose acetate, Arnel®, and Acele®; polyamides such as Nylons (e.g., Nylon 6, Nylon 66, Nylon 610 and the like; polyesters such as Fortrel®, Kodel®, and the polyethylene terephthalate fibers, Dacron®; polyolefins such as polypropylene, polyethylene; polyvinyl acetate fibers and mixtures thereof.

Non-woven substrates made from natural materials consist of webs or sheets most commonly formed on a fine wire screen from a liquid suspension of the fibers. Substrates made from natural materials useful in the present invention can be obtained from a wide variety of commercial sources.

Non-woven substrates made from synthetic material useful in the present invention can also be obtained from a wide variety of commercial sources, such as e.g. Sontaro® 8868, a hydro-entangled material, containing about 50% cellulose and about 50% polyester, and having a basis weight of about 60 gsy or 2.2 oz per sq. yard, having rectangular apertures of about 1.5 mm by 2 mm in dimension with about 150 to 160 apertures per sq. inch, available from Dupont Chemical Corp; PGI Laveft fabric, a 2.35 oz/sq. yd., 63% rayon/29% PET/8% binder fabric with rectangular apertures of about 2 mm×3 mm in dimension having about 40 to 45 apertures per square inch from PGI Corporation; Carlee high loft fabric, 2.0 oz/sq.yd., 100% polyester fabric from Carlee Corporation; and KC 5A high loft fabric, approx. 2.5 oz per sq. yard, 100% polyester fabric from Kimberly Clark Corporation.

Most preferred as a component substrate for purposes of this invention are non-woven substrates, especially blends of rayon/polyester and ratios of 10:90 to 90:10, preferably ratios of 20:80 to 80:20, optimally 40:60 to 60:40 by weight. A most useful substrate is a 70:30 rayon/polyester non-woven wipe article.

Anywhere from 1 to 100, preferably from 5 to 50 single wipes may be stored within a dispensing pouch or container, preferably a moisture impermeable pouch or container. During storage and between dispensing, the pouch or container is preferably resealable. Single wipe containing pouches may also be employed.

Wet Flexibility

The inventive dry cleansing wipe is characterized by having wet flexibility or in other words, the ability of the wipe to substantially return to its original shape after being crushed, while saturated with water during use. Substantially returning to its original shape is herein defined as the single apertured fabric returning to at least 30 percent, preferably 40 percent of its original z-axis dimension using a stepwise loading and unloading bulk test as described below. Techniques to impart wet flexibility to woven and non-woven fabrics are well known in the art. Art recognized methods to improve wet flexibility of non-wovens include 1) increasing the level of latex, acrylic, or other binders; 2) laminating two or more fabrics together; 3) employing longer and/or stiffer fibers; 4) employing larger diameter fibers; or 5) modifying the manufacturing processes such as by employing needle-punching to form a stiffer fabric, or the like.

Apertured Fabrics

The inventive dry cleansing wipe requires at least one apertured fabric, where a pattern is created by a network of bundled fiber segments surrounding apertures or holes; or in a contiguous nonwoven web which has been apertured or provided with slits or other openings. In one preferred embodiment, the water insoluble matterial is a substantially contiguous network of water insoluble fibers having a plurality of macroscopic openings. A macroscopic opening is defined as an opening that is large relative to the intrinsic pore size of the water insoluble material.

In a typical spunbond or bonded carded web, for example, a macroscopic opening would appear to the eye to be a deliberately introduced hole or void in the web rather than a characteristic pore between adjacent fibers, and specifically could have a characteristic width of about 0.1 mm to about 5 mm, or larger; preferably about 1 mm to about 5 mm. A useful characteristic width may be defined as 4 times the area of the aperture divided by the perimeter. Useful fabric aperture densities are about 10 to 700 per square inch, preferably about 20 to 500 per square inch.

As discussed above, the nonwoven web may be made from synthetic fibers, as is known in the art, and may be a spunbond web, a meltblown web, a bonded carded web, or other fibrous nonwoven structures known in the art. For example, a polyester nonwoven web such as a low basis weight spunbond material could be provided with apertures through pin aperturing; perf embossing and mechanical stretching of the web; die punching or stamping to provide apertures or holes in the web; hydroentangling to impart apertures by rearrangement of the fibers due to the interaction of water jets with the fibrous web as it resides on a patterned, textured or three-dimensional substrate that imparts a pattern to the web; water knives that cut out desired apertures or holes in the web; laser cutters that cut out portions of the web; patterned forming techniques, such as air laying of synthetic fibers on a patterned substrate to impart macroscopic openings; needle punching with sets of barbed needles to engage and displace fibers; and other methods known in the art. Preferably, the openings are provided in a regular pattern over at least a portion of an outersheet of the absorbent article.

The water insoluble substrates or fabrics of the present invention can comprise two or more layers, each having a different texture and abrasiveness. The differing textures can result from the use of different combinations of materials or from the use of a substrate having a more abrasive side for exfoliation and a softer, absorbent side for gentle cleansing. In addition, separate layers of the substrate can be manufactured to have different colors, thereby helping the user to further distinguish the surfaces.

The apertured fabric or sheet may be bonded to at least one other nonwoven sheet of water insoluble fibers ("second sheet") by lamination, adhesives, stitching, fasteners, or other art recognized binding methods. Preferably, the second sheet is attached to the apertured sheet by means of lamination, adhesives and related agents, including hot melts, latexes, glues, starch, waxes, and the like, which adhere or join the upper regions of the apertured sheet with adjacent portions of the second sheet. Preferably, adhesives are applied only to the most elevated portions of the apertured sheet to effect the bonding between the apertured sheet and the second sheet, leaving the apertures substantially free of adhesive. Adhesive application can be through meltblown application of hot melt glues and thermoplastic materials, spray or swirl nozzles of melted or dissolved adhesives, printing of adhesive material onto one or both surfaces before joining, and the like. If adhesives are applied directly to the apertured sheet by means of spray, mist, aerosol, or droplets in any form, prior to contact of the apertured sheet with the water insoluble matter, then it is desirable to use a template or patterned shield to prevent application of adhesive to the apertures to avoid clogging. Preferably, the second sheet is composed of polyester or a polyester and cellulose blend, does not contain apertures and has the characteristics of high loft, a basis weight of about 1 to 5 ounces per square yard, preferably about 2 to 3 ounces per square yard and optionally contains a binder. Useful binders include latex or acrylic materials added to the fabric between about 5 to 40 weight percent of the fabrics total weight, preferably between about 5 to 25 weight percent.

Lathering Surfactant

The inventive wipe also contains a lathering surfactant. By a "lathering surfactant" is meant a surfactant, which when combined with water and mechanically agitated generates a foam or lather. Preferably, these lathering surfactants should be mild, which means that they must provide sufficient cleansing or detersive benefits but not overly dry the skin or hair, and yet meet the lathering criteria described above.

The products of the present invention typically comprise a lathering surfactant to substrate weight ratio between about 0.005 to 2, preferably between about 0.05 to 1, more preferably from about 0.1 to 0.5.

A wide variety of lathering surfactants are useful herein and include those selected from the group consisting of anionic, nonionic, cationic, amphoteric and lathering surfactant mixtures thereof.

Among the anionic lathering surfactants useful herein are the following non-limiting examples which include the classes of:

(1) Alkyl benzene sulfonates in which the alkyl group contains from 9 to 15 carbon atoms, preferably 11 to 14 carbon atoms in straight chain or branched chain configuration. Especially preferred is a linear alkyl benzene sulfonate containing about 12 carbon atoms in the alkyl chain.

(2) Alkyl sulfates obtained by sulfating an alcohol having 8 to 22 carbon atoms, preferably 12 to 16 carbon atoms. The alkyl sulfates have the formula $ROSO_3—M^+$ where R is the $C_{8-22}$ alkyl group and M is a mono- and/or divalent cation.

(3) Paraffin sulfonates having 8 to 22 carbon atoms, preferably 12 to 16 carbon atoms, in the alkyl moiety. These surfactants are commercially available as Hostapur SAS from Hoechst Celanese.

(4) Olefin sulfonates having 8 to 22 carbon atoms, preferably 12 to 16 carbon atoms. Most preferred is sodium $C_{14}$–$C_{16}$ olefin sulfonate, available as Bioterge AS 40 ®.

(5) Alkyl ether sulfates derived from an alcohol having 8 to 22 carbon atoms, preferably 12 to 16 carbon atoms, ethoxylated with less than 30, preferably less than 12, moles of ethylene oxide. Most preferred is sodium lauryl ether sulfate formed from 2 moles average ethoxylation, commercially available as Standopol ES-2 ®.

(6) Alkyl glyceryl ether sulfonates having 8 to 22 carbon atoms, preferably 12 to 16 carbon atoms, in the alkyl moiety.

(7) Fatty acid ester sulfonates of the formula: $R^1CH(SO_3–M+)CO_2R^2$ where $R^1$ is straight or branched alkyl from about C8- to C18, preferably C12 to C16, an d$R^2$ is straight or branched alkyl from about $C_1$ to C6, preferably primarily $C_1$, and M+ represents a mono- or divalent cation.

(8) Secondary alcohol sulfates having 6 to 18, preferably 8 to 16 carbon atoms.

(9) Fatty acyl isethionates having from 10 to 22 carbon atoms, with sodium cocoyl isethionate being preferred.

(10) Dialkyl sulfosuccinates wherein the alkyl groups range from 3 to 20 carbon atoms each.

(11) Alkanoyl sarcosinates corresponding to the formula RCON(CH$_3$)CH$_2$CH$_2$CO$_2$M wherein R is alkyl or alkenyl of about 10 to about 20 carbon atoms and M is a water-soluble cation such as ammonium, sodium, potassium and trialkanolammonium. Most preferred is sodium lauroyl sarcosinate.

(12) Alkyl lactylates wherein the alkyl groups range from 8 to 18 carbon atoms, with sodium lauryl lactylate sold as Pationic 138 C® available from the Patterson Chemical Company as the most preferred.

(13) Taurates having from 8 to 16 carbon atoms, with cocoyl methyl taurate being preferred.

Nonionic lathering surfactants suitable for the present invention include C$_{10}$–C$_{20}$ fatty alcohol or acid hydrophobes condensed with from 2 to 100 moles of ethylene oxide or propylene oxide per mole of hydrophobe; C$_2$–C$_{10}$ alkyl phenols condensed with from 2 to 20 moles of alkylene oxides; mono- and di-fatty acid esters of ethylene glycol such as ethylene glycol distearate; fatty acid monoglycerides; sorbitan mono- and di-C$_8$–C$_{20}$ fatty acids; and polyoxyethylene sorbitan available as Polysorbate 80 and Tween 80® as well as combinations of any of the above surfactants.

Other useful nonionic surfactants include alkyl polyglycosides, saccharide fatty amides (e.g. methyl gluconamides) as well as long chain tertiary amine oxides. Examples of the latter category are: dimethylododecylamine oxide, oleyldi(2-hydroxyethyl)amine oxide, dimethyloctylamine oxide, dimethyldecylamine oxide, dimethyltetradecylamine oxide, di(20-hydroxyethyl)tetradecylamine oxide, 3-didodecyoxy-2-hydroxypropyldi(3-hydroxypropyl)amine oxide, and dimethylhexadecylamine oxide.

Amphoteric lathering surfactants useful for the present invention include aliphatic secondary and tertiary amines, preferably wherein the nitrogen is in a cationic state, in which the aliphatic radicals can be straight or branched chain and wherein one of the radicals contains an ionizable water solubilizing group such as carboxy, sulphonate, sulphate, phosphate or phosphonate. Illustrative substances are cocoamidopropyl betaine, cocoamphoacetate, cocoamphodiacetate, cocoamphopropionate, cocoamphodipropionate, cocoamidopropyl hydroxysultaine, cetyl dimethyl betaine, cocoamidopropyl PG-dimonium chloride phosphate, coco dimethyl carboxymethyl betaine, cetyl dimethyl betaine and combinations thereof.

The amount of lathering surfactant to substrate weight ratio is between about 0.005 to 2, preferably between about 0.05 to 1, more preferably from about 0.1 to 0.5.

A humectant is optionally incorporated with compositions of the present invention. Humectants are normally polyols. Representative polyols include glycerin, diglycerin, polyalkylene glycols and more preferably alkylene polyols and their derivatives including propylene glycol, dipropylene glycol, polypropylene glycol, polyethylene glycol and derivatives thereof, sorbitol, hydroxypropyl sorbitol, hexylene glycol, 1,2-butylene glycol, 1,2,6-hexanetriol, isoprene glycol, ethoxylated glycerol, propyoxylated glycerol and mixtures thereof. The most preferred is 2-methyl-1,3-propanediol available as MP Diol from the Arco Chemical Company. Amounts of the polyol may range from about 0.5 to about 95%, preferably from about 1 to about 50%, more preferably from about 1.5 to 20%, optimally from about 3 to about 10% by weight of the deposited composition.

Impregnating compositions of the present invention may also include silicones of a volatile and non-volatile variety. Typical volatile silicones are the cyclomethicones commercially available as Dow Corning 244, 245, 344 and 345. Linear volatile dimethicones are also suitable. Non-volatile silicones include polydimethyl siloxanes of a viscosity greater than 2 centistoke and silicone copolyols also known as dimethicone copolyol for which Dow Corning 193 is a commercial source. Amounts of the silicones may range from about 0.01 to about 20, preferably from about 0.5 to about 3% by weight of the deposited composition.

Cationic conditioning agents in monomeric and polymeric type are also useful for purposes of this invention. Examples of the polymeric type include: cationic cellulose derivatives, cationic starches, copolymers of a diallyl quaternary ammonium salt and an acryl amide, quaternized vinylpyrrolidone, vinylimidazole polymers, polyglycol amine condensates, quaternized collagen polypeptide, polyethylene imine, cationized silicone polymer (e.g. Amodimethicone), cationic silicone polymers provided in a mixture with other components under the trademark Dow Corning 929 (cationized emulsion), copolymers of adipic acid and dimethylaminohydroxypropyl diethylenetriamine, cationic chitin derivatives, cationized guar gum (e.g. Jaguar C-B-S, Jaguar C-17, Jaguar C-16 etc. manufactured by the Celanese Company), quaternary ammonium salt polymers (e.g. Mirapol A-15, Mirapol AD-1, Mirapol AZ-1, etc., manufactured by the Miranol Division of the Rhone Poulenc Company). Most preferred is polyquaternium-11 available as Luviquat® PQ 11 sold by the BASF Corporation.

Examples of monomeric cationic conditioning agents are salts of the general structure:

Wherein R$^1$ is selected from an alkyl group having from 12 to 22 carbon atoms, or aromatic, aryl or alkaryl groups having from 12 to 22 carbon atoms; R$^2$, R$^3$, and R$^4$ are independently selected from hydrogen, an alkyl group having from 1 to 22 carbon atoms, or aromatic, aryl or alkaryl groups having from 12 to 22 carbon atoms; and X$^-$ is an anion selected from chloride, bromide, iodide, acetate, phosphate, nitrate, sulfate, methyl sulfate, ethyl sulfate, tosylate, lactylate, citrate, glycolate, and mixtures thereof. Additionally, the alkyl groups can also contain ether linkages, or hydroxy or amino group substituents (e.g. the alkyl groups can contain polyethylene glycol and polypropylene glycol moieties). Preferably the anion is phosphate, especially preferred is hydroxy ethyl cetyl dimonium phosphate available as Luviquate® Mono CP from the BASF Corporation.

Amino silicone quats may similarly be employed. Most preferred is Silquat AD designated by the CTFA as Silicone Quaternium 8, available from Siltech Inc.

Amounts of each cationic agent may range from about 0.01 to 5%, preferably from about 0.1 to about 3%, optimally from about 0.3 to about 2.5% by weight of the deposited composition.

The disposable, single use personal care cleansing products of the present invention are manufactured by separately or simultaneously adding onto or impregnating into a water insoluble substrate a lathering surfactant and a fatty acid, wherein the resulting product is substantially dry. By "separately" is meant that the surfactants and fatty acids can be added sequentially, in any order without first being combined together. By "simultaneously" is meant that the surfactants and fatty acids can be added at the same time, with or without first being combined together.

The surfactant, fatty acids and any optional ingredients can be added onto or impregnated into the water insoluble substrate by any means known to those skilled in the art. For example, addition can be through spraying, laser printing, splashing, dipping, soaking, or coating.

When water or moisture is used or present in the manufacturing process, the resulting treated substrate is then dried so that it is substantially free of water. The treated substrate can be dried by any means known to those skilled in the art. Non-limiting examples of known drying means include the use of convection ovens, radiant heat sources, microwave ovens, forced air ovens, and heated rollers or cams. Drying also includes air drying without the addition of heat energy, other than that present in the ambient environment. Also, a combination of various drying methods can be used.

Manufacture of Wipes Impregnated with Aqueous Liquid Composition

The treated, dry wipe articles of the present invention are manufactured by adding onto or impregnating into the apertured sheet, an aqueous liquid composition containing a lathering surfactant, a structurant or volatile solvent, and optionally a water insoluble functional agent.

Techniques for coating or impregnating the apertured sheet are well known in the art and are not elaborated on here. Preferably, the aqueous liquid composition of the present invention is coated on by means of a process comprising spraying, printing, splashing, dipping, soaking, flood coating, spray coating or metered dosing. More specialized techniques, such as Meyer Rod, floating knife or doctor blade may also be used herein.

After the coating or impregnating and optionally drying in the case where a volatile solvent is employed, the lathering surfactant to substrate weight ratio is between about 0.005 to 2, preferably between about 0.05 to 1, more preferably from about 0.1 to 0.5.

Prior to or after impregnation of the aqueous liquid composition into the apertured sheet, the sheet may be folded into stacks. The sheet is then typically packaged in any of the moisture and vapor impermeable packages known in the art.

Method of Using the Treated Wipe Articles

For treatment of the user's skin or hair, the treated wipe is saturated with water, manipulated manually to generate a lather, and is applied to a surface (e.g., a skin surface) via topical application to release or deposit an effective amount of the aqueous liquid composition to perform the desired cleansing or other function. The amount of water-insoluble functional ingredient delivered from the wipe and frequency of topical application can vary widely, depending upon the individual user's needs. With respect to personal application to the skin, such application can range from about once per day to about four times daily, preferably from about twice per day to about three times daily. Number of wipes used per application can range from I to about 4 wipes, preferably I to about 2 wipes. The amount of water-insoluble functional ingredient deposited on each wipe is generally from about 3.5 mg to about 175 mg per wipe. The treated wipes of the present invention can also be used prophylactically by administrating to healthy skin surfaces to guard from or prevent undesired skin conditions and/or infections using the dosing regimen described above.

Except in the operating and comparative examples, or where otherwise explicitly indicated, all numbers in this description indicating amounts of material ought to be understood as modified by the word "about".

The following examples will more fully illustrate the embodiments of this invention. All parts, percentages and proportions referred to herein and in the appended claims are by weight unless otherwise illustrated.

EXAMPLE 1

Cleansing articles according to the present invention may have facial cleansing compositions as outlined under Tables 1–3. 0.75 grams of the composition of Table 3 was placed on various individual 6 by 8 inch apertured substrate, dried in an oven, and the dynamic lather coefficients were measured as described below. Apertures were made in a sample of non-apertured Buckeye 6009 for evaluation purposes. Non-apertured Buckeye 6009 was used as a control for the Dynamic Lather Coefficient determination.

| Fabric | Apertures-Diameter and density (mm and no./sq. in.) | Dynamic Lather Coefficient[1] | | Wet Flexi-bility (%) | Lather Character |
|---|---|---|---|---|---|
| | | Initial | Exhaustion | | |
| Inventive: | | | | | |
| PGI | 2–3; 40–45 | 1.61 | 2.61 | 47.1 | Rich, bubbly |
| Comparative: | | | | | |
| Buckeye 6009 | N/A | 1.00 | 1.00 | 6.7 | Airy |
| Buckeye 6009 | 4; 8–10 | 1.29 | 1.29 | 6.7 | Airy |
| Oil of Olay ® normal to oily[2] | N/A | 0.73 | 0.86 | 13.7 | Runny |
| Oil of Olay ® normal to dry | 2–3; 20–24 | 0.73 | 0.86 | 28.0 | Runny |

[1]Control Buckeye 6009 non-apertured initial lather volume is 130 mls and exhaustion lather volume is also 130 mls.
[2]Oil of Olay ® wipes were tested without further modification.

Tables 1–3

Compositions according to Tables 1–3 are prepared in the following manner. Hexyleneglycol, betaine and polyquaternium 7 are mixed together under moderate to vigorous agitation. Thereafter decyl polyglucoside, sarcosinate, lactylate, and triglycerides are added separately until dissolved while heating the reactor at 80° C. under agitation. The resultant composition is cooled to 60° C. whereupon the silicone quaternary ammonium salt is blended into the composition. Fragrance and preservatives are folded into the composition after the latter has been cooled to 45° C. A six inch by eight inch single apertured sheet of one gram is then loaded with 0.75 grams of the composition of Table 1 and 3 with no drying, and 1.2 grams of the composition of Table 2 followed by oven drying.

Tables 4–5

The compositions according to Tables 4 and 5 are prepared in the following manner: Hexylene Glycol, polymer JR400, hydroxy methyl cellulose, Sodium laureth sulfate, and lauryl alcohol are all mixed together under moderate to vigorous agitation while the reactor is maintained at 80° C. Citric acid is then added to adjust the pH to 5.5. Next methylchloroisothiazolione and caprylic/capric triglycerides are dissolved and the blend is allowed to cool to 45° C. after which the fragrance is then added.

Table 6

The composition according to table 6 is prepared in the following manner: stearic acid is heated to 160 to 170° F. and 5% of it is neutralized with sodium hydroxide. The blend is then heated to 180 to 200° F. and sodium cocyl isethionate is added with agitation, next PEG 8000, betaine, glycerin and sunflower seed oil are added with agitation. Fragrance is then added after the blend is cooled to 45° C.

Table 7

The composition according to table 7 is prepared in the following manner: stearic acid, maltodextrin, PEG 300, and water are blended together at a temperature of 160 to 170° F., sodium cocyl isothionate is then added at a temperature of 180 to 200° F., PEG 8000 is then added followed by the betaine, glycerin and the mixture is allowed to cool to below 170° F. and then sunflower seed oil is added. Lastly fragrance is added after the blend is cooled to 45° C.

EXAMPLE 2

Cleansing articles according to the present invention may contain cleansing compositions as outlined under Tables 4–7. In the following example, 4.8 grams of the composition according to Table 4 is placed on various individual apertured water insoluble substrates that are thereafter laminated to individual, non-apertured, high-loft, water insoluble substrates as described below. The dynamic lather coefficients were measured of both (A) the individual apertured coated fabric alone and (B) the laminated article as an average of 3 replicates of initial lather volume measurement and 3 replicates of total lather volume measurement until exhaustion of lather production from the article.

Results

A) Single Fabric

| Fabric | Apertures-Diameter (mm) and no./sq. inch | Dynamic Lather Coefficient Initial[3] | Exhaustion[3] | Lather |
|---|---|---|---|---|
| Inventive | | | | |
| PGI | 2–3; 40–45 | 1.43 | 1.48 | Rich bubbly |
| Dupont 8868 | 1.5–2; 150–160 | 1.41 | 1.48 | Rich bubbly |
| Comparative | | | | |
| Carlee | N/A | 1.43 | 1.35 | |
| Felix 7027 | N/A | 1.00 | 1.00 | Loose bubbly |
| Diamond | N/A | 1.72 | 1.51 | Airy bubbly |
| CLC 059 | N/A | 0.98 | 0.95 | Runny bubbly |
| CLC 062 | N/A | 1.50 | 1.67 | Loose, runny bubbly |
| NC 008 | N/A | 1.70 | 2.05 | Very Airy |
| KC-5A | N/A | 1.31 | 1.14 | |

[3]Control Felix 7021 initial lather volume is 135 mls and exhaustion lather volume is 415 mls.

Fabric Description

List of Fabrics, Content and Texture:

| Fabric Name | Appearance | Basis wt. And Type |
|---|---|---|
| PGI, Lavett | 7 holes per linear inch Rectangular apertures about 2–3 mm; 40–45 per sq. in. | 2.35 oz/sq. yd., 63% rayon/29% PET/8% binder |
| Dupont 8868 | 13 holes per linear inch Rectangular apertures about 1.5–2 mm; 150–160 per sq. in. | 2.2 oz/sq. yd., 50% wood pulp/50%polyester |
| Carlee high loft | High loft, non-apertured | 2.0 oz/sq. yd., 100% polyester |
| Felix 7027 from PGI | Flat, non-apertured | 2.3 oz/sq. yd., 65% rayon/35% polyester |
| Diamond KK105 from Miratec | Raised textured, non-apertured | 2.9 oz/sq. yd., 50 cotton/50% polyester |
| CLC 059 from Miratec | Flat, non-apertured | 3.3 oz/sq/yd., 100% rayon |
| CLC 062 from Miratec | Flat, non-apertured | 3 oz/sq. yd., 50% rayon/50% PET |
| NC 008 from Miratec | Flat, non-apertured | 3 oz/sq. yd., 100% polyester |
| KC 5A from Kimberly Clark | High loft, non-apertured | Approx. 2.5 oz/sq. yd., 100% polyester |
| Buckeye #6009 | Flat, non-apertured and with hand made apertures | 2.3 oz/sq. yd., wood pulp |

B) Laminated Fabric

| Fabric | Dynamic Lather Coefficient Initial[4] | Exhaustion[4] | Lather |
|---|---|---|---|
| Inventive: (apertured) | | | |
| PGI/Carlee | 1.19 | 1.28 | Creamy, bubbly |
| Dupont 8868/Carlee | 1.25 | 1.66 | Creamy, rich, thick |
| KC-5A/PGI | 1.21 | 1.16 | Bubbly |
| CLC 059/PGI | 0.99 | 1.25 | Bubbly, runny |
| Comparative: (non-apertured) | | | |
| Felix/Carlee | 1.00 | 1.00 | Bubbly, loose |
| Diamond/Carlee | 1.10 | 1.42 | Rich, creamy, some bubbles |
| CLC 059/Carlee | 0.93 | 1.23 | Creamy, airy, bubbles |
| NC 008/Carlee | 0.88 | 1.34 | Creamy, bubbly |
| CLC 062/Carlee | 0.99 | 1.64 | Creamy |

[4]Control Felix 7021/Carlee high loft laminate initial lather volume is 192 mls and exhaustion lather volume is 688 mls Experimental Test Methods:

Wet Flexibility

Wet flexibility of the impregnated substrates were evaluated using the following test procedure: samples were submersed in a pan of water for about 2 seconds and the excess water was removed by contacting the sample on both sides with blotter paper. The sample was then placed in a bulk testing device and the sample thickness or z-axis distance was measured at increasing incremental loads of 0.10 to 3.0 PSI followed by decreasing incremental loads of 2.5 to 0.10 PSI. The % wet flexibility (or % z-axis recovery) was calculated by dividing the z-axis recovery distance by the z-axis maximum compression displacement distance, the result then multiplied by 100. The z-axis recovery distance was obtained as the difference in height between the unloaded sample recovery height and the sample height at 3.0 PSI loading.

TABLE 1

Solution A

| Ingredient Name | W/W % |
|---|---|
| Hexylene Glycol | 16.26 |
| Polyquaternium 7, 95% | 1.07 |
| Cocamidopropyl betaine, 82% active | 17.60 |

TABLE 1-continued

Solution A

| Ingredient Name | W/W % |
| --- | --- |
| Decyl polyglucoside | 36.09 |
| Sodium lauryl sarcosinate, 94% active | 17.60 |
| Sodium Lauryl lactylate | 1.65 |
| Capric/caprylic triglycerides | 2.50 |
| Silicone quaternum-8, 40% | 6.63 |
| Fragrance | 0.40 |
| DMDM hydantoin and iodopropynyl butylcarbamate in butylene glycol | 0.20 |

TABLE 2

Solution B

| Ingredient Name | W/W % |
| --- | --- |
| water | 10.20 |
| PEG 9 M | 1.00 |
| Cocamidopropyl betaine, 30% | 30.00 |
| Decyl glucoside 50% | 20.00 |
| Sodium lauroyl sarcosinate 30% | 30.00 |
| Hydroxyethyl cetyldimonium phosphate 40% | 2.00 |
| Sodium Lauryl lactylate | 1.00 |
| Polyquaternium 11, 30% | 1.00 |
| Silicone quaternium-8, 40% | 4.00 |
| Fragrance | 0.60 |
| DMDM hydantoin and iodopropynyl butylcarbamate in butylene glycol | 0.20 |

TABLE 3

Solution B2

| Ingredient Name | W/W % |
| --- | --- |
| Hexylene glycol | 16.26 |
| Polyquaternium 7, 95% | 1.07 |
| Cocamidopropyl betaine, 82% | 17.60 |
| Decyl glucoside 50% | 36.09 |
| Sodium lauroyl sarcosinate 94% | 17.60 |
| Sodium Lauryl lactylate | 1.65 |
| Capric/caprylic triglycerides | 2.50 |
| Silicone quaternium-8, 40% | 6.63 |
| Fragrance | 0.40 |
| DMDM hydantoin and iodopropynyl butylcarbamate in butylene glycol | 0.20 |

TABLE 4

Solution C

| Ingredient Name | W/W % |
| --- | --- |
| Hexylene Glycol | 39.61 |
| Polymer JR400 | 0.25 |
| Hydroxy Methyl Cellulose | 0.38 |
| Sodium Laureth sulfate | 35.71 |
| Cocoamido propyl betaine | 12.20 |
| Sodium lauryl sulfate | 7.73 |
| Lauryl alcohol | 0.50 |
| Citric acid (pH adjustment) | 0.10 |
| Methylchloroisothiazolione/methylisothiazolinone | 0.02 |
| Caprylic/capric triglycerides - fractionated coconut oil | 2.50 |
| Fragrance | 1.00 |

TABLE 4-continued

Solution C

| Ingredient Name | W/W % |
| --- | --- |
| Physical properties | |
| Viscosity (50° C.) | <5000 cps |
| pH | 5.5 |

TABLE 5

Solution D

| Ingredient Name | W/W % |
| --- | --- |
| Hexylene Glycol | 28.31 |
| Polymer JR400 | 0.30 |
| Hydroxy Methyl Cellulose | 0.45 |
| Sodium Laureth sulfate | 42.86 |
| Cocoamido propyl betaine | 14.63 |
| Sodium lauryl sulfate | 9.28 |
| Lauryl alcohol | 0.60 |
| Citric acid (pH adjustment) | 0.05 |
| Methylchloroisothiazolione/methylisothiazolinone | 0.02 |
| Caprylic/capric triglycerides - fractionated coconut oil | 2.50 |
| Fragrance | 1.00 |
| Physical properties | |
| Viscosity (50° C.) | <5000 cps |
| PH | 5.5 |

TABLE 6

Solution E

| Ingredient Name | W/W % |
| --- | --- |
| ASAD - stearic acid | 0.00 |
| Sodium Cocyl isethionate | 50.00 |
| PEG 8000 | 37.91 |
| Cocoamidopropyl betaine | 4.83 |
| Glycerine | 3.23 |
| Sunflower seed oil | 3.23 |
| Fragrance | 0.80 |

TABLE 7

Solution F

| Ingredient Name | W/W % |
| --- | --- |
| ASAD - Stearic acid | 5.00 |
| Maltodextrin | 0.67 |
| PEG 300 | 0.14 |
| Water | 0.19 |
| Sodium Cocyl isethionate | 50.00 |
| PEG 8000 | 31.91 |
| Cocoamidopropyl betaine | 4.83 |
| glycerine | 3.23 |
| Sunflower seed oil | 3.23 |
| Fragrance | 0.80 |

Latherability Test Methods:

The lather depicted in FIGS. 5(a), (b), (c); 6(a) and (b) and described in Table 2 (A) and (B) was generated by wetting the sample with warm running water and repeatedly squeezing the sample for approx. 3 to 4 seconds.

Dynamic Lather volume coefficients were calculated as the ratio of the sample lather volume to that of a control for Examples 1 and 2. The control for Example 1 was the Buckeye 6009 flat wood pulp, non-apertured fabric. The control for Example 2A was the Felix 7027 flat, non-apertured fabric, and for Example 2B was the same Felix fabric laminated with a Carlee high loft fabric.

A traditional Lather Volume (Funnel Method) test was employed. The test involved two large sinks and a measuring funnel of 10.5 inch diameter and a 100 ml graduated cylinder with the bottom cleanly removed. The cylinder was fitted with a 0 ml mark over the funnel stem. The cylinder was then sealed to the funnel. The procedure involved placing the funnel on the bottom of sink #1. Distilled water was added to the sink until the 0 ml mark of the funnel. Tap water was added (~120 ppm water hardness) to sink #2 until the water level reached the 0 ml mark of the funnel. A desired temperature of 95–103° F. is then set. The sample is placed under running tap water at 95–103° F. and soaked for about 5 seconds to condition the sample. The sample is then held between both hands under running the water and rotated for ten half turns to start forming lather. The sample is then rotated by hand for fifteen half turns to build up lather. The sample is then laid aside and the hands are worked to increase lather for 10 seconds. A funnel is then placed over the hands with both being placed into sink #1. When hands are fully immersed, they are slid from under the funnel. The funnel is lowered to the bottom of the sink with lather volume being read. The value recorded is designated the initial lather volume. The process is repeated and the lather volumes recorded until no further lather is seen. The total lather volume is then summed and designated the exhaustion lather volume. The foregoing description and examples illustrate selected embodiments of the present invention. In light thereof variations and modifications will be suggested to one skilled in the art, all of which are within the scope and spirit of this invention.

We claim:

1. A disposable, single use, personal care cleansing product, comprising:
   (i) a water insoluble substrate;
   (ii) a lathering surfactant;
   (iii) said product having a wet flexibility of at least 30%; wherein the water insoluble substrate comprises at least one sheet selected from non-woven, woven, hydro-entangled or air entangled substrates and wherein the product is substantially dry prior to use.

2. A method of cleansing the skin or hair with a personal cleansing product comprising:
   (i) a water insoluble substrate;
   (ii) a lathering surfactant;
   (iii) said product having a wet flexibility of at least 30%; wherein the water insoluble substrate comprises at least one sheet selected from non-woven, woven, hydro-entangled or air entangled substrates; and
   wherein the product is substantially dry prior to use.

3. The article of claim 1 wherein the water insoluble substrate includes at least one layer of an apertured sheet, said apertures having an average diameter along said aperture's major axis of between about 0.1 mm to 1.0 cm.

4. The article of claim 3 wherein the average diameter along said aperture's major axis is between about 1 to 5 mm.

5. A disposable, single use, personal care cleansing product, comprising:
   (i) a water insoluble substrate;
   (ii) a lathering surfactant;
   (iii) said product having a wet flexibility of at least 30% and a dynamic lather volume coefficient of at least about 1.4; wherein the water insoluble substrate comprises at least one sheet selected from non-woven, woven, hydro-entangled or air entangled substrates; and
   wherein said product is substantially dry prior to use.

6. The article of claim 5 wherein said water insoluble substrate has at least one apertured sheet.

7. The article of claim 6 wherein said apertured sheet has a plurality of apertures having an average major diameter and an average minor diameter; said average major diameter having a value between about 0.5 mm to 1.0 cm.

8. The article of claim 7 wherein said average major diameter has a value between about 1 to 5 mm and said average minor diameter has a value between about 1 to 5 mm.

9. The article of claim 1 wherein the lathering surfactant and substrate weight ratio is between about 0.005 to 2.

10. The article of claim 9 wherein said weight ratio is in the range of about 0.1 to 0.5.

11. The article of claim 1 wherein said lathering surfactant is selected from the group consisting of anionic, amphoteric, or nonionic surfactants, and mixtures thereof.

12. The article of claim 11 wherein said lathering surfactant comprises at least one betaine and at least one sarcosinate surfactant.

13. The article of claim 5 wherein the water insoluble substrate comprises at least one apertured sheet and at least one non-apertured sheet bonded to said at least one apertured sheet.

14. The article of claim 13 wherein said at least one non-apertured sheet contains less than about 1.0 weight ratio of a lathering surfactant to substrate.

15. The article of claim 5 wherein said wet flexibility is greater than about 40%.

16. A method of manufacturing a disposable, single use, personal care cleansing product comprising the steps of:
   impregnating a water insoluble substrate wherein the water insoluble substrate comprises at least one sheet selected from non-woven, woven, hydro-entangled or air entangled substrates with a composition including a lathering surfactant in a surfactant to substrate ratio range of about 0.005 to about 2; and
   drying said impregnated substrate until said cleansing product contains less than about 0.15 weight ratio of water to substrate;
   wherein said dried substrate has a wet flexibility of at least about 30%.

17. The method of claim 16 wherein said dried substrate has a wet flexibility of at least about 40%.

18. The method of claim 16 wherein the surfactant to substrate weight ratio range is about 0.1 to 0.5.

19. The method of claim 2 wherein said personal cleansing product has a dynamic lathering volume coefficient of at least 1.4.

* * * * *